United States Patent
Avikainen et al.

(10) Patent No.: US 8,444,821 B2
(45) Date of Patent: May 21, 2013

(54) MEASURING OF WEB

(75) Inventors: Marko Avikainen, Jyväskylä (FI); Petri Niemi, Jyväskylä (FI); Heikki Kettunen, Espoo (FI); Markku Mäntylä, Kangasala (FI); Heimo Keränen, Oulu (FI)

(73) Assignee: Metso Automation Oy, Helsinki (FI)

( * ) Notice: Subject to any disclaimer, the term of this patent is extended or adjusted under 35 U.S.C. 154(b) by 0 days.

(21) Appl. No.: 12/810,365

(22) PCT Filed: Dec. 30, 2008

(86) PCT No.: PCT/FI2008/050793
§ 371 (c)(1),
(2), (4) Date: Sep. 1, 2010

(87) PCT Pub. No.: WO2009/083655
PCT Pub. Date: Jul. 9, 2009

(65) Prior Publication Data
US 2010/0319866 A1 Dec. 23, 2010

(30) Foreign Application Priority Data
Dec. 31, 2007 (FI) .................................... 20075975

(51) Int. Cl.
*G01N 21/89* (2006.01)
*G01B 11/30* (2006.01)
*G01B 11/25* (2006.01)
*D21F 7/06* (2006.01)
*G06T 7/00* (2006.01)

(52) U.S. Cl.
USPC ........... 162/198; 162/252; 162/253; 162/263; 73/105; 250/341.1; 250/339.11; 250/559.01; 250/559.45; 356/237.1; 356/237.2; 356/429; 356/433; 356/445; 356/600

(58) Field of Classification Search
USPC ............ 162/198, 252, 263; 250/341.1–341.2, 250/339.1–339.11, 559.01, 559.45; 356/237.1–237.2, 429–430, 432–433, 445, 356/600, 623, 631; 73/105
See application file for complete search history.

(56) References Cited

U.S. PATENT DOCUMENTS
3,922,093 A * 11/1975 Dandliker et al. ............. 356/600
4,092,068 A * 5/1978 Lucas et al. ..................... 356/73
(Continued)

FOREIGN PATENT DOCUMENTS
DE 100 63 293 A1 7/2002
EP 0 076 866 A1 4/1983
(Continued)

OTHER PUBLICATIONS
NanoLED Brochure, "The reliable source of ultrashort optical pulses," Jobin Yvon, no dated.*
(Continued)

*Primary Examiner* — Jose A Fortuna
(74) *Attorney, Agent, or Firm* — Oliff & Berridge, PLC

(57) ABSTRACT

Optical radiation sources functioning on different optical bands radiate on different optical bands and focus optical radiation on a region in a web surface as pulses in such a manner that illumination areas of the pulses overlap on the plane of the web. At most one optical radiation band is focused on the web from the direction of the normal. The spatial intensity distribution of at least one optical band differs from the uniform distribution and the intensity distributions of at least two different optical bands differ from one another in a predetermined manner. A camera forms still images of the web surface region on each optical radiation band. An image-processing unit determines the surface topography of the web on the basis of the images. In addition, a controller may control the paper manufacturing process on the basis of the determined surface topography.

50 Claims, 6 Drawing Sheets

U.S. PATENT DOCUMENTS

Figure 1:
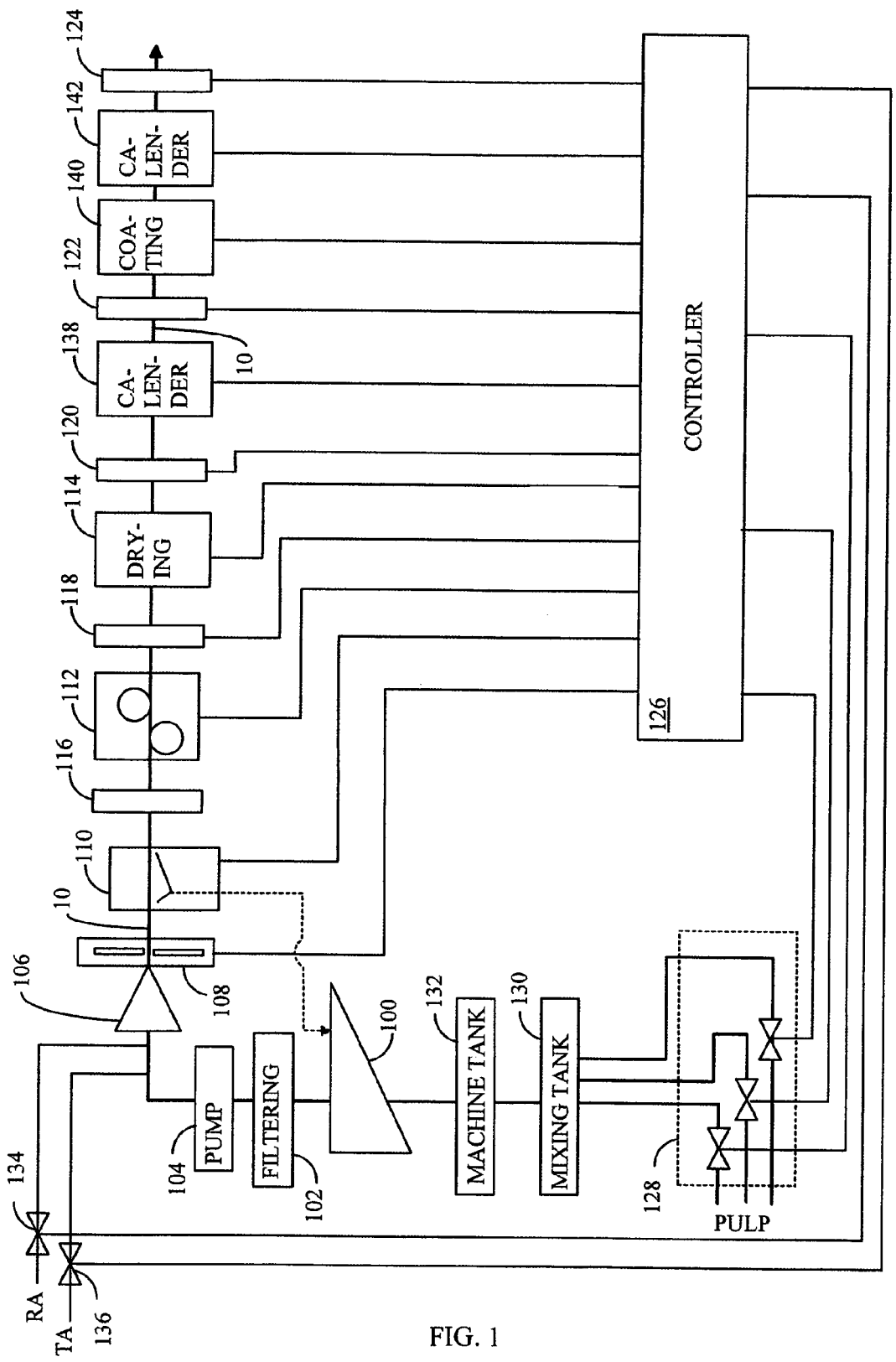

| | | | |
|---|---|---|---|
| 4,349,277 A | 9/1982 | Mundy et al. | |
| 4,490,618 A * | 12/1984 | Cielo | 250/559.01 |
| 5,608,527 A * | 3/1997 | Valliant et al. | 356/600 |
| 5,614,662 A * | 3/1997 | Hallan et al. | 73/105 |
| 5,654,799 A * | 8/1997 | Chase et al. | 356/600 |
| 5,684,707 A | 11/1997 | Rogowski | |
| 6,252,623 B1 | 6/2001 | Lu et al. | |
| 6,495,831 B1 * | 12/2002 | Hyvarinen et al. | 250/339.07 |
| 6,549,286 B2 * | 4/2003 | Komulainen et al. | 356/600 |
| 7,114,377 B2 * | 10/2006 | Lindig | 73/105 |
| 7,295,299 B2 * | 11/2007 | Schmalfuss | 356/237.2 |
| 7,889,342 B2 * | 2/2011 | Hellstrom et al. | 356/429 |
| 7,936,464 B2 * | 5/2011 | Keranen | 356/623 |
| 8,117,891 B2 * | 2/2012 | Graeffe et al. | 73/1.81 |
| 2001/0015414 A1 | 8/2001 | Keranen et al. | |
| 2002/0039187 A1 | 4/2002 | Keranen | |
| 2002/0113975 A1 * | 8/2002 | Komulainen et al. | 356/600 |
| 2002/0134523 A1 * | 9/2002 | Mantyla et al. | 162/263 |
| 2002/0152630 A1 | 10/2002 | Lindsay et al. | |
| 2002/0196415 A1 | 12/2002 | Shiratani | |
| 2003/0047135 A1 * | 3/2003 | Kansakoski et al. | 118/665 |
| 2003/0132387 A1 * | 7/2003 | Tenhunen et al. | 250/339.11 |
| 2004/0233421 A1 * | 11/2004 | Weinhold | 356/237.1 |
| 2006/0077400 A1 | 4/2006 | Zwemer et al. | |
| 2006/0164645 A1 * | 7/2006 | Hietanen et al. | 356/430 |
| 2006/0232790 A1 * | 10/2006 | Chase et al. | 356/614 |
| 2007/0035733 A1 * | 2/2007 | Reich et al. | 356/430 |
| 2009/0056412 A1 * | 3/2009 | Graeffe et al. | 73/1.81 |
| 2009/0135434 A1 * | 5/2009 | Keranen | 356/611 |
| 2009/0151435 A1 * | 6/2009 | Moore | 73/105 |
| 2010/0045988 A1 * | 2/2010 | Hietanen et al. | 356/430 |
| 2010/0165344 A1 * | 7/2010 | Kokko et al. | 356/429 |
| 2010/0296107 A1 * | 11/2010 | Keranen | 356/623 |
| 2010/0319866 A1 * | 12/2010 | Avikainen et al. | 162/192 |

FOREIGN PATENT DOCUMENTS

| | | |
|---|---|---|
| FI | 20001568 | 12/2001 |
| JP | 54151067 A * | 11/1979 |
| WO | WO 2009083655 A1 * | 7/2009 |

OTHER PUBLICATIONS

International Search Report issued in International Application No. PCT/FI2008/050793 dated Apr. 28, 2009.

Written Opinion of the International Preliminary Examining Authority issued in International Application No. PCT/FI2008/050793 dated Jan. 20, 2010.

* cited by examiner

MEASURING OF WEB

FIELD

The invention relates to a measuring and control method, and a measuring and control system.

BACKGROUND

Measurements of a web and a paper surface at the manufacturing stage are important to ensure that the surface, printability and quality of the end product, i.e. paper, in general meet the production demands.

The surface topography of ready-made paper or paper under manufacture may be measured in various ways. For instance, a Bendtsen measuring device according to the standard SCAN-P21:67 may be used to determine the surface roughness, whereby a sample is put onto a glass plate and a measuring head producing compressed air is set on top of the sample. The amount of flowing air is measured, and the measurement is repeated at least 20 times at different points of the paper sample. The rougher the sample is, the more air is flowing, and thus the surface roughness can be measured on the basis of the flow rate.

The surface topography has also been measured optically. In this case, the measurement can be carried out based on, for instance, light scattering or by employing photometric stereo photography.

Optical radiation, such as light, can be focused on the sample surface and the intensity of the scattered light can be measured from different directions. The intensity of the optical radiation scattered in different directions depends on the roughness of the surface.

In a stereo measurement, two images of the surface are formed, taken from different directions. By combining the images as one three-dimensional image, it is also possible to illustrate the surface variation in the depth direction. The size of surface irregularities and the direction of the shapes may thus be measured from the image.

These measurements are nevertheless related with problems. The Bendtsen measurement is slow and not suitable for an on-line measurement. Also, surface topography is not the only factor affecting the Bendtsen measurement, wherefore the measurement does not describe the nature or scale of the surface topography. Measurements of optical radiation scattering may well be proportioned to the Bendtsen measurement but neither the Bendtsen measurement nor the measurement of scattering describes the nature or scale of the surface topography.

A photometric stereo measurement, for its part, is slow and complex because, among other things, two images taken from different directions must be combined.

BRIEF DESCRIPTION

It is an object of the invention to provide an improved measuring method, control method as well as measuring and control systems implementing the method. This is achieved by a measuring method for a moving web, comprising focusing optical radiation on the web within a predetermined time window determining the smallest distinguishable detail of the web. The method also comprises focusing radiation of at least two different optical bands on a region in the web surface as pulses in such a manner that illumination areas of the pulses overlap at least partly on the plane of the web, at most one optical radiation band is focused on the web from the direction of the normal, the spatial intensity distribution of at least one optical band differs from the uniform distribution and the intensity distributions of at least two different optical bands differ from one another in a predetermined manner; forming pulse-based images of said web region on said bands of at least two different optical radiations; and determining the surface topography of the web on the basis of at least two images formed on the bands of different optical radiations.

The invention also relates to a control method for a paper manufacturing process, the method comprising focusing optical radiation on a moving web within a predetermined time window determining the smallest distinguishable detail of the web. The method further comprises focusing radiation of at least two different optical bands on a region in the web surface as pulses in such a manner that illumination areas of the pulses overlap at least partly on the plane of the web, at most one optical radiation band is focused on the web from the direction of the normal, the spatial intensity distribution of at least one optical band differs from the uniform distribution and the intensity distributions of at least two different optical bands differ from one another in a predetermined manner; forming pulse-based images of said web region on said bands of at least two different optical radiations; and determining the surface topography of the web on the basis of at least two images formed on the bands of different optical radiations; and controlling the paper manufacturing process on the basis of the determined surface topography.

The invention also relates to a measuring system for a moving web, wherein the system is arranged to focus optical radiation on the web within a predetermined time window determining the smallest distinguishable detail of the web. The system comprises at least two optical radiation sources, a camera, and an image-processing unit, of which at least two optical radiation sources radiate on different optical bands; and each optical radiation source is arranged to focus optical radiation on a region in the web surface as pulses in such a manner that illumination areas of the pulses are arranged to overlap at least partly on the plane of the web, at most one optical radiation band is arranged to be focused on the web from the direction of the normal, the spatial intensity distribution of at least one optical band is arranged to differ from the uniform distribution and the intensity distributions of at least two different optical bands are arranged to differ from one another in a predetermined manner; the camera is arranged to form, on each optical radiation band, images of the web surface region on which the radiation of at least two different optical bands is focused; and the image-processing unit is arranged to determine the surface topography of the web on the basis of at least two images formed on the bands of different optical radiations.

The invention also relates to a measuring system for a moving web, wherein the system is arranged to focus optical radiation on the web within a predetermined time window determining the smallest distinguishable detail of the web. The system comprises at least two means for emitting optical radiation, a means for forming an image and a means for processing an image, of which the at least two means for emitting optical radiation radiate on different optical bands; and each means for emitting optical radiation is arranged to focus optical radiation on a region in the web surface as pulses in such a manner that illumination areas of the pulses are arranged to overlap at least partly on the plane of the web, at most one optical radiation band is arranged to be focused on the web from the direction of the normal, the spatial intensity distribution of at least one optical band is arranged to differ from the uniform distribution and the intensity distributions of at least two different optical bands are arranged to differ from one another in a predetermined manner; the means for forming an image is arranged to form, on each optical radiation band, images of the web surface region on which the radiation of at least two different optical bands is focused; and the means for processing an image is arranged to determine the surface topography of the web on the basis of at least two images formed on the bands of different optical radiations.

The invention also relates to a control system for a paper manufacturing process, the method comprising focusing optical radiation on a moving web within a predetermined time window determining the smallest distinguishable detail of the web. The system comprises at least two optical radiation sources, a camera, an image-processing unit, and a controller, of which at least two optical radiation sources radiate on different optical bands; and each optical radiation source is arranged to focus optical radiation on a region in the web surface as pulses in such a manner that illumination areas of the pulses are arranged to overlap at least partly on the plane of the web, at most one optical radiation band is arranged to be focused on the web from the direction of the normal, the spatial intensity distribution of at least one optical band is arranged to differ from the uniform distribution and the intensity distributions of at least two different optical bands are arranged to differ from one another in a predetermined manner; the camera is arranged to form, on each optical radiation band, images of the web surface region on which the radiation of at least two different optical bands is focused; the image-processing unit is arranged to determine the surface topography of the web on the basis of at least two images formed on the bands of different optical radiations; and the controller is arranged to control the paper manufacturing process on the basis of the determined surface topography.

The invention further relates to a control system for a paper manufacturing process, the method comprising focusing optical radiation on a moving web within a predetermined time window determining the smallest distinguishable detail of the web. The system comprises at least two means for emitting optical radiation, a means for forming an image and a means for processing an image, of which the at least two means for emitting optical radiation radiate on different optical bands; and each means for emitting optical radiation is arranged to focus optical radiation on a region in the web surface as pulses in such a manner that illumination areas of the pulses are arranged to overlap at least partly on the plane of the web, at most one optical radiation band is arranged to be focused on the web from the direction of the normal, the spatial intensity distribution of at least one optical band is arranged to differ from the uniform distribution and the intensity distributions of at least two different optical bands are arranged to differ from one another in a predetermined manner; the means for forming an image is arranged to form, on each optical radiation band, images of the web surface region on which the radiation of at least two different optical bands is focused; and the means for processing an image is arranged to determine the surface topography of the web on the basis of at least two images formed on the bands of different optical radiations; and a control means is arranged to control the paper manufacturing process on the basis of the determined surface topography.

Preferred embodiments of the invention are described in the dependent claims.

The method and system of the invention provide a plurality of advantages. Measurement is fast and rather simple, wherefore it is suitable for on-line use. The solution allows efficient control of the manufacturing process from pulp to an end product.

LIST OF FIGURES

Figure 2A:
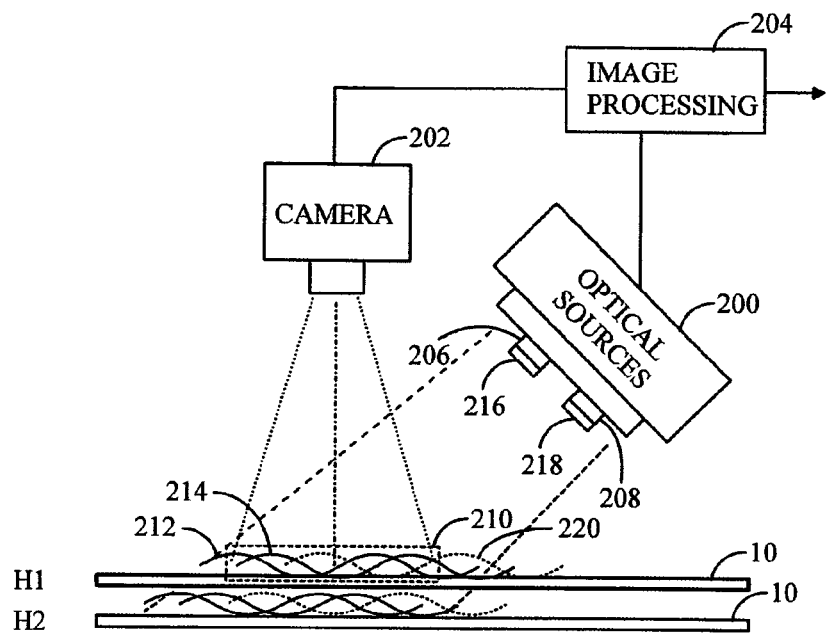
Figure 2B:
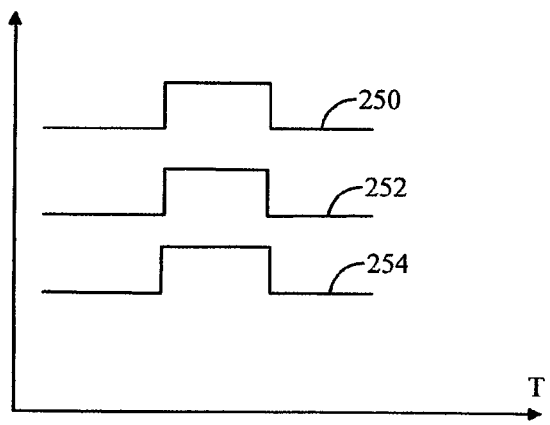
Figure 2C:
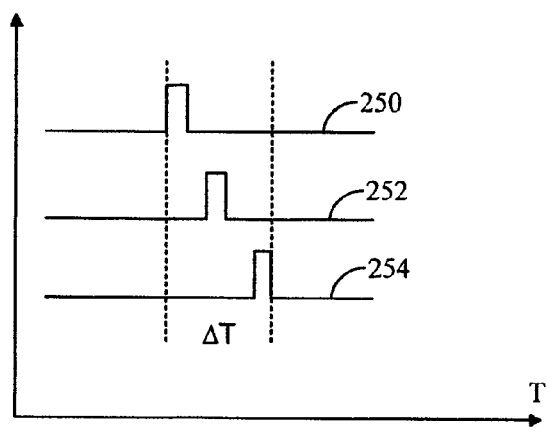
Figure 3A:
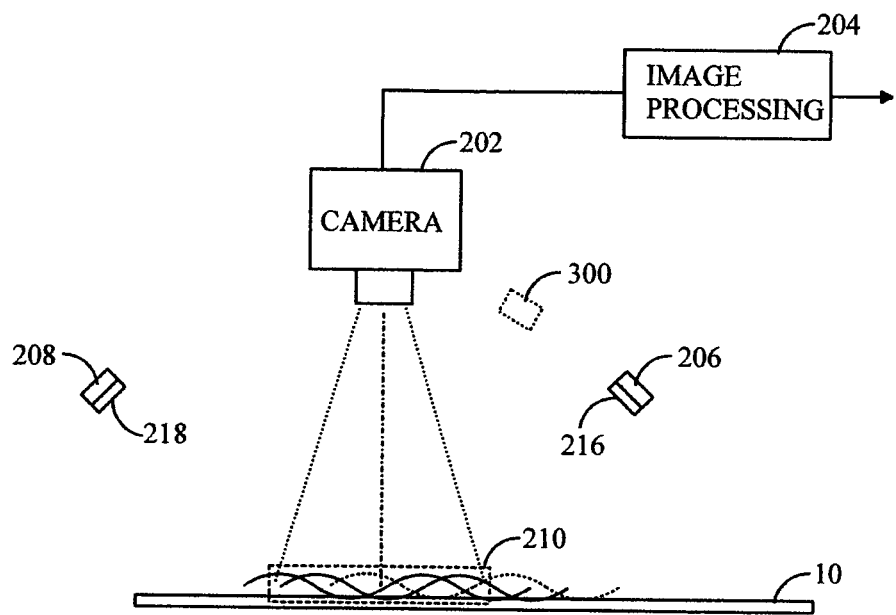
Figure 3B:
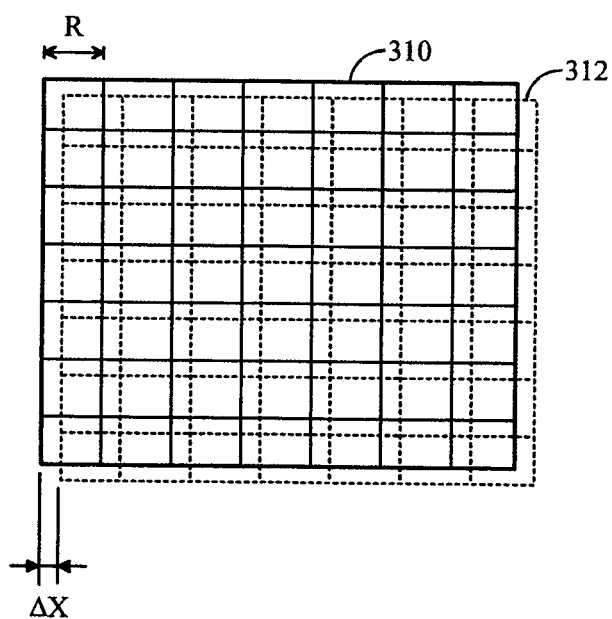
Figure 4:
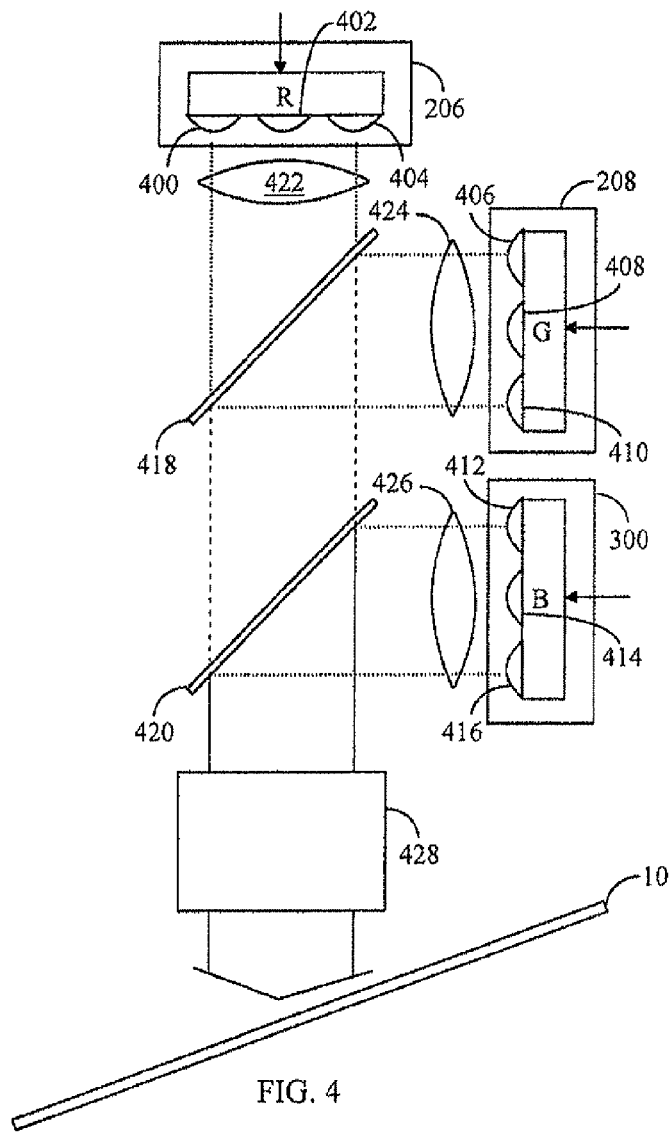
Figure 5:
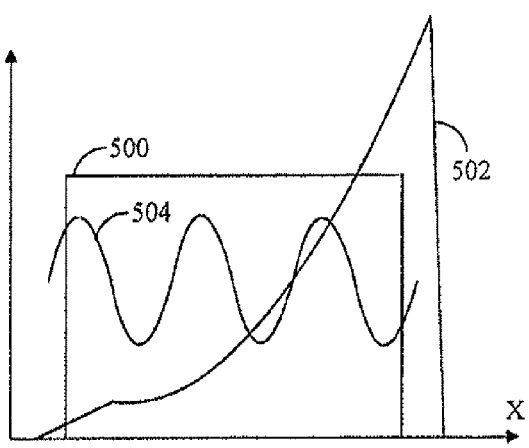
Figure 6:
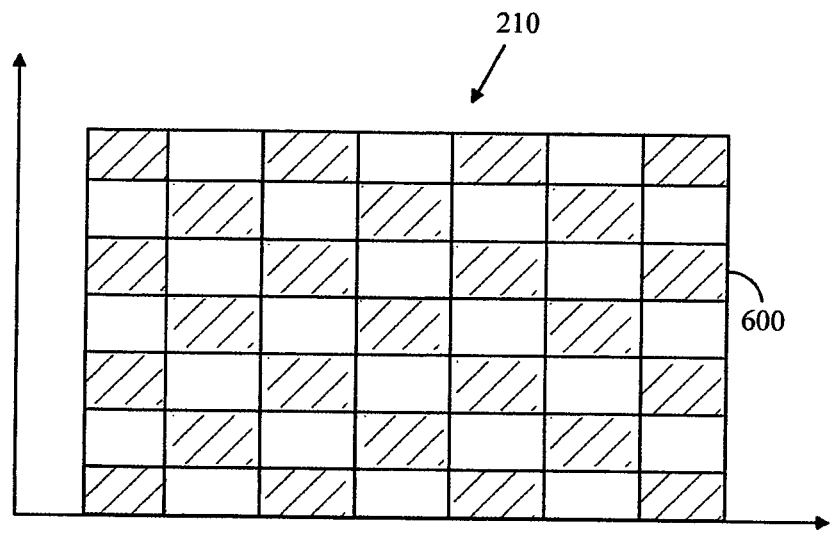
Figure 7:
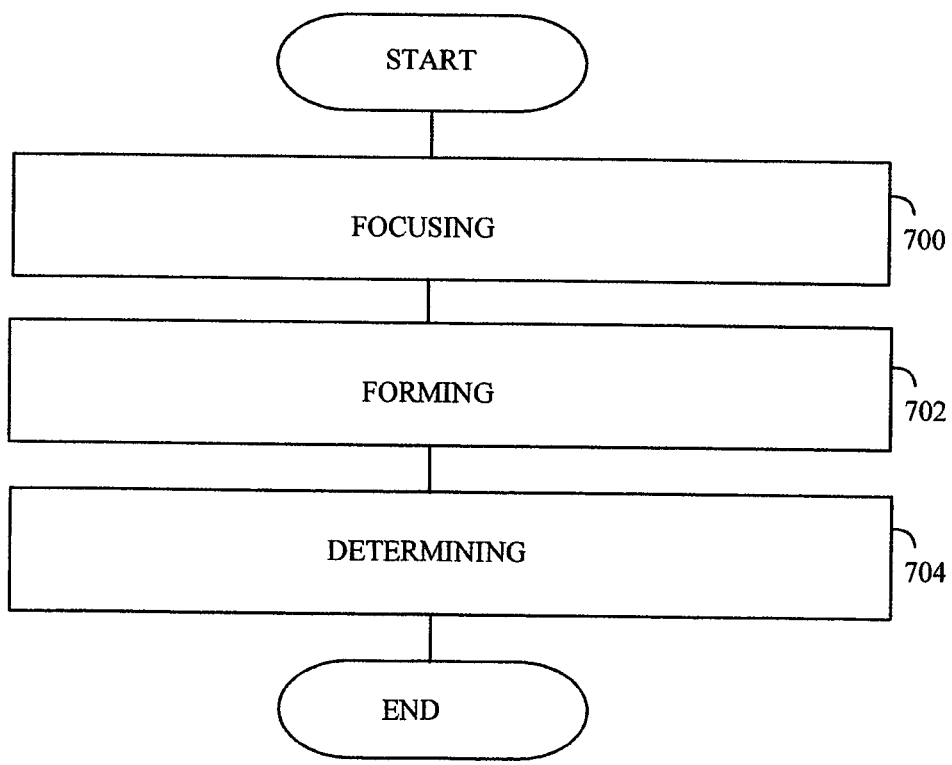
Figure 8:
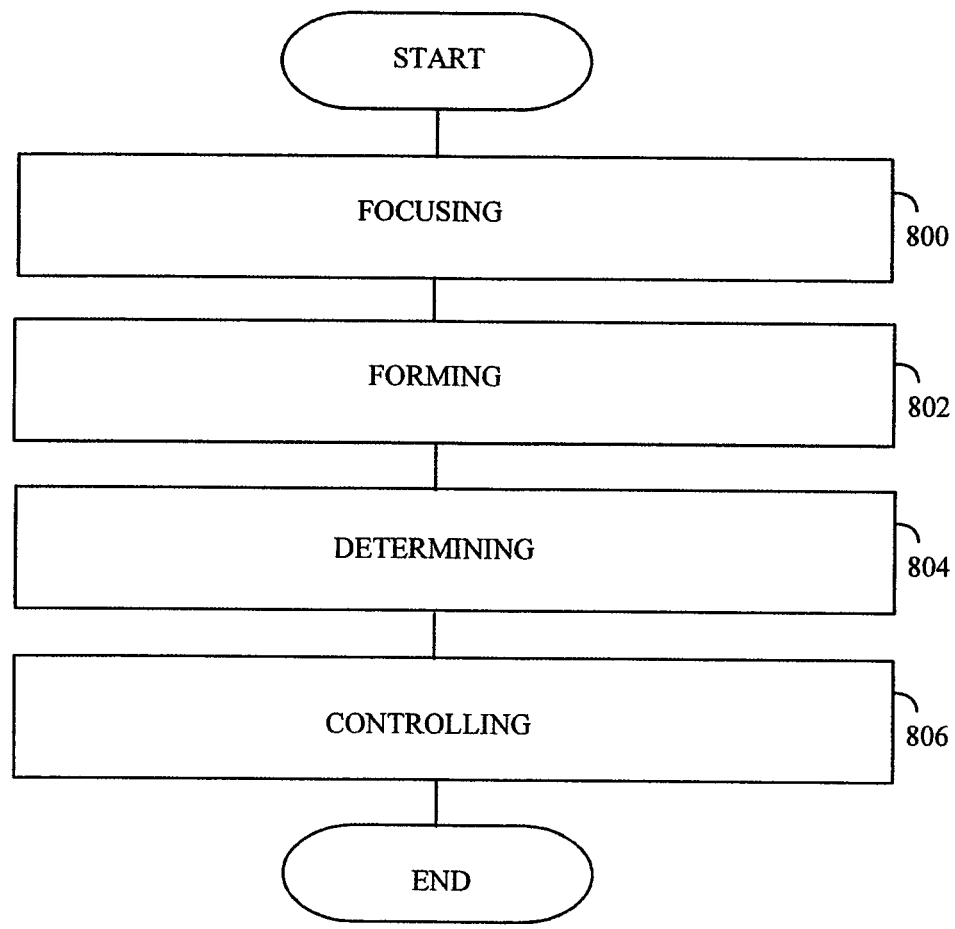

The invention will now be described in closer detail in association with the preferred embodiments and with reference to the attached drawings, in which FIG. 1 shows a paper machine, FIG. 2A illustrates a measuring principle, in which the illumination is focused from one direction, FIG. 2B shows pulses having approximately the same duration, FIG. 2C shows short, non-simultaneous pulses within the same time window, FIG. 3A illustrates a measuring principle, in which the illumination is focused from a plurality of directions, FIG. 3B shows images formed at two different wavelengths and having an inaccurate alignment with respect to one another, FIG. 4 shows a solution employing chromatic mirrors, FIG. 5 illustrates spatial intensity distributions, FIG. 6 illustrates a two-dimensional intensity distribution, FIG. 7 shows a flow chart of a measuring method, and FIG. 8 shows a flow chart of a control method.

DESCRIPTION OF EMBODIMENTS

FIG. 1 shows the principle structure of a paper machine. A pulp flow or a plurality of pulp flows is/are fed into the paper machine through a wire pit 100, which is usually preceded by a mixing tank 130 for pulp flows and a machine tank 132. Machine pulp is batched for a short circulation by a weight control or a grade change program. The mixing tank 130 and the machine tank 132 may also be replaced by a separate mixing reactor (not shown in FIG. 1) and the batching of machine pulp is controlled by feeding each pulp flow separately by means of valves or some other flow control means 128. In the wire pit 100, the machine pulp is mixed with water to provide the short circulation (a broken line from a former 110 to the wire pit 100) with a desired consistency. From the pulp thus produced, it is possible to remove sand (hydrocyclones), air (deaeration tank) or other rough material (pressure screen) by cleaning equipment 102, and pulp is pumped by means of a pump 104 into a head box 106. Before the head box 106, if desired, a filler TA, such as kaolin clay, calcium carbonate, talc, chalk, titanium oxide, silica, etc., and/or a retention agent RA, such as inorganic, natural organic or synthetic water-soluble organic polymers may be added to the pulp. The filler may be used to improve formation, surface properties, opacity, brightness and printability and to reduce manufacturing costs. The retention agents RA, for their part, increase the retention of fines and fillers and simultaneously speed up the dewatering in a manner known per se. Both the fillers and the retention agents thus affect the surface topography of the web and the paper.

From the head box 106, the pulp is fed through a slice 108 of the head box into the former 110, which may be a fourdrinier or a gap former. In the former 110, the web 10 is dewatered and ash, fines and fibres are removed into the short circulation. In the former 110, the pulp is fed as a web 10 onto the wire, and the web 10 is preliminarily dried and pressed in a press 112. The web 10 is primarily dried in a drying section 114. There is usually at least one measuring part 116 to 124, by which for instance the surface topography of the web 10 can be measured.

A paper machine, which in this application refers to both paper and cardboard machines and also to pulp manufacturing machines, may also comprise, for instance, a precalender 138, a coating part/section 140 and/or a post-calender 142.

However, there is not necessarily any coating section 140, and in that case there are not necessarily more than one calender 138, 142. In the coating section 140, a coating colour, which may contain for example kaolin, chalk or carbonate, starch, and/or latex, may be applied onto the paper surface. The use of coating colour usually reduces the roughness of the paper and improves glossiness.

In the calenders 138, 142, in which an uncoated or coated paper web travels between rolls that press with a desired force, the surface topography of the paper, such as roughness, can be changed. The calender 138, 142 may also affect the thickness and/or gloss of the paper. In the calender 138, 142, the properties of the paper web may be changed by moistening the web or by means of temperature and nip load/pressure between the rolls so that the greater the press applied to the web is, the smoother and glossier the paper will become. Moistening and an increase in the temperature further reduce roughness and improve glossiness. In addition, it is obvious that the operation of a paper machine is known per se to a person skilled in the art, wherefore it is not described in more detail in this context.

FIG. 1 also shows a control system for the paper machine. Factors affecting the quality and grade change include the amount and ratio of pulp flows, amount of filler, amount of retention agent, machine velocity, amount of backwater and drying capacity. A controller 126 may control the batching of pulp flows by means of valves 128, the batching of the filler TA by a valve 136, the batching of the retention agent RA by a valve 134, it may also control the size of the slice 108, the machine velocity, the amount of backwater and the drying process in block 114. The controller 126 also utilizes the measuring devices 116 to 120 for monitoring control measures, quality and/or grade change. The controller 126 may also measure the web 10 properties elsewhere (e.g. at the same points where controls are carried out).

The controller 126 may be considered as a control arrangement based on automatic data processing of the paper machine, or as a part thereof. The controller 126 may receive digital signals or convert the received analog signals to digital signals. The controller 126 may comprise a microprocessor and memory and process the signal according to a suitable computer program. The controller 126 may be based on a PID (Proportional-Integral-Derivative), MPC (Model Predictive Control) or GPC (General Predictive Control) control, for example.

FIG. 2A illustrates the measuring principle of the web 10. A projector 200, a camera 202 and an image-processing unit 204 may be used in the measurement. In FIG. 2A, the projector 200 comprises two optical radiation sources 206, 208 radiating on different optical bands towards the web 10 from at least approximately the same direction, and the illumination areas of these radiations overlap at least partly in a space where the web 10 is located at the time of measurement. Generally, there may be even more optical radiation sources 206, 208. Optical radiation refers in this application to electro-magnetic radiation, the wavelength of which is about 50 nm to 500 μm. Optical wavelength bands used for the measurement must not overlap completely, but the band of at least one source comprises, as a band used for the measurement, at least one wavelength that is not comprised in the bands of other sources. Instead of only one wavelength, the optical band may also comprise a wavelength range, which may have a width of hundreds or even (several dozens or hundreds of) thousands of nanometers.

At least one optical radiation source 206, 208 may be a radiation source based on a semiconductor material, such as a LED. Optical radiation sources acting at different wavelengths may comprise at least two LEDs at different wavelengths. Instead of one LED, each optical radiation source 206, 208 may also comprise a group of LEDs.

At least one optical radiation source 206, 208 may be a laser, the lasering material of which being a solid material, a liquid or a gas, for instance. The laser of a solid material may be based on a semiconductor material, for example.

Let us first consider that the surface of the web 10 is at a height H1. Different optical radiation sources 206, 208 of the projector 200 focus, on the plane of the web 10 in a common illumination area, optical radiation on a region 210 of the web 10 surface as pulses. Different optical radiation sources 206, 208 focus radiation on the web 10 on several different bands with known spatial intensity distributions. Each pulse on a different optical band is supposed to be so short that the web does not seem to move at all during the optical pulse, or the movement during the optical pulse is shorter than the desired resolution of the image. If the web 10 moves at a velocity V=2000 m/min ≈33 m/s and the smallest details that need to be distinguished have a size of R=10 μm or more, the duration $\Delta T$ must be shorter than R/V, i.e. $\Delta T<(10\ \mu m)/(33\ m/s)\approx 0.3$ μs. However, it is often enough that the longest possible pulse duration is at most 2 μs, but sometimes it may be necessary to require that the longest possible pulse duration does not exceed 1 μs. If the optical sources 206, 208 can produce optical pulses which are at least rather short (dozens or hundreds of nanoseconds, for example) compared to the required greatest possible pulse duration (e.g. 1 μs), the different optical sources 206, 208 may produce non-simultaneous pulses to the web 10 within a predetermined time window (i.e. during the longest possible pulse duration). The pulses may in this case be entirely non-simultaneous or partly simultaneous. However, the pulses are focused on the same region 210 of the web 10, because in terms of the measurement, the web 10 does not move significantly during the time of different pulses or the time between them.

FIG. 2B shows three at least approximately simultaneous pulses 250, 252, 254 at different wavelengths, the duration $\Delta T$ of which is almost the same as R/V. FIG. 2C, for its part, shows three non-simultaneous pulses 250, 252, 254 at different wavelengths, the duration of each being substantially shorter than RN but all being within the time window of $\Delta T<R/V$.

Besides the duration of optical radiation, it is required that the intensity of the band of at least one optical source 206, 208 is not uniformly distributed spatially and that the intensity distributions of the bands of at least two different optical sources 206, 208 differ from one another in a predetermined manner. The intensity distributions of two different optical sources 206, 208 may differ from one another in almost any way and also partly resemble each other. The intensity distributions may also differ from one another, for instance, in that they are orthogonal, uncorrelated and/or independent with respect to each other. As shown in FIG. 2A, the intensity distribution of the first optical band 212 may follow the shape of a sine wave. The intensity distribution of the second optical band 214 may also follow the shape of a sine wave but it may be phase-shifted 120° ($2\pi/3$ radian) with respect to the first optical band.

If also a third optical radiation source is used, the intensity distribution of the third optical band 220 may have the shape of a sine wave but it is still phase-shifted 120° with respect to the first and second bands. Instead of a sinusoidal spatial modulation, the intensity in said at least one spatial intensity distribution of the optical band may vary periodically in some other way, too.

Let us consider that the surface of the web 10 is at a height H2. Since the optical radiation is focused at an oblique angle onto the surface of the web 10, the shift of the web 10 surface in the vertical direction (from height H1 to height H2, for instance) moves the intensity distributions of each optical band in the horizontal direction. The shift of the web 10 surface may be local or extensive. A local shift may be caused by irregularities on the web 10 surface, which need to be examined by a topography measurement.

The camera 202, the shutter of which may be open all the time or during the time of the pulses or longer, may form, based on the pulses, on each optical radiation band images of the region 210 on the web 10 surface on which the radiation of at least two different optical bands is focused. The function for controlling the mechanical shutter of the camera may be implemented by an electrical exposure control. Successive images can be formed by repeatedly flashing optical radiation pulses at different wavelengths. When the camera 202 functions with visible light, it may deal with an RGB (Red-Green-Blue) camera capable of forming images in three different colours. Generally an RGB camera comprises three detector matrices (or vectors), each of which may be sensitive to one colour of the base forming the chromatic coordinate system.

The image-processing unit 204 may determine the surface topography of the web 10 on the basis of at least two different simultaneous images formed on the optical radiation band. The intensity difference between the images in each surface region of which the camera has formed an image changes if the web moves in the height direction. However, the change is not identical for each pixel. Thus, if the intensities of the images differ, it is interpreted to result from the height differences in the surface topography of the measured surface. The image-processing unit 204 may thus determine the surface topography of the web 10 on the basis of differences in the intensity variations in different still pictures.

When the intensities of different optical radiations vary sinusoidally and have a phase shift of 120°, the signal processing may be carried out, for example, as follows.

In a sinusoidal projection method, three sine patterns are projected onto the surface to be examined on three different wavelength bands at an incident angle that is oblique to the surface normal, and an image is formed of the surface to be examined with a camera that forms separate images on each wavelength band. The sine patterns are implemented so that the sine patterns projected on different wavelength bands are at different phases. The phase difference of the sine patterns may be 120°, for instance. The three images formed with the camera may be expressed mathematically in the form:

$$I_1(i) = I_0(i)\{1 + m(i)\cos[\phi(i) + \delta_1]\} \quad (1)$$

$$I_2(i) = I_0(i)\{1 + m(i)\cos[\phi(i) + \delta_2]\} \quad (2)$$

$$I_3(i) = I_0(i)\{1 + m(i)\cos[\phi(i) + \delta_3]\} \quad (3)$$

where i is the pixel index of the image, $I_0$ is the intensity of background radiation, m is the modulation amplitude, $\phi$ is the phase to be determined, and $\delta_1$, $\delta_2$ and $\delta_3$ are phase constants. If $\delta_1$, $\delta_2$ and $\delta_3$ are known, the tangent of the phase $\phi$ can be determined on the basis of formula (1):

$$\tan(\phi) = \frac{(I_3 - I_2)\cos(\delta_1) + (I_1 - I_3)\cos(\delta_2) + (I_2 - I_1)\cos(\delta_3)}{(I_3 - I_2)\sin(\delta_1) + (I_1 - I_3)\sin(\delta_2) + (I_2 - I_1)\sin(\delta_3)}$$

wherein the phase $\phi$ can be determined by means of the arcus tangent function of basic trigonometry:

$$\phi = \arctan\left(\frac{(I_3 - I_2)\cos(\delta_1) + (I_1 - I_3)\cos(\delta_2) + (I_2 - I_1)\cos(\delta_3)}{(I_3 - I_2)\sin(\delta_1) + (I_1 - I_3)\sin(\delta_2) + (I_2 - I_1)\sin(\delta_3)}\right)$$

After $\phi$ has been determined, the height alternation $\Delta h$ relating to the surface topography may be formed, for instance, on the basis of the equation $$\Delta h = \frac{\varphi}{2\pi} \frac{\Lambda}{\tan\alpha}$$

where $\Lambda$ is the period of the projected sine pattern and $\alpha$ is the incident angle of illumination to the surface normal.

A predetermined intensity difference may be formed in such a manner that each optical radiation source 206, 208 comprises an intensity shaper 216, 218, which is arranged to produce, in at least one web surface direction, an intensity distribution varying in a known manner and differing in a predetermined manner on different optical radiation bands.

Each intensity shaper 216, 218 may form a structural pattern and each intensity shaper 216, 218 may thus be, for example, a mask comprising a predetermined transmission pattern. The intensity shaper 216, 218 may alternatively be a reflection mask comprising a predetermined transmission pattern. In this case, different optical radiation sources 206, 208 focus structural radiation on the web 10 by projecting the predetermined patterns on the optical bands onto the web 10, parallel-shifted a predetermined distance with respect to one another. The pattern of each optical radiation determines the spatial intensity distribution of the optical radiation. The intensity of at least one optical band varies along the surface of the web 10 in at least one dimension in a known manner. The intensity may also vary two-dimensionally. The predetermined patterns on different optical bands may be parallel-shifted a predetermined distance with respect to one another to make the intensity distributions of different optical radiations on the web 10 surface different.

FIG. 3A shows an embodiment, in which—differing from the solution of FIG. 2A—the bands of different optical radiations are focused on the web 10 from different directions. Thus, for instance, the optical radiation source 206 focuses optical radiation on its own band onto the web 10 obliquely from the right side, and the optical radiation source 208 focuses optical radiation of its own band on the web 10 obliquely from the left side. In addition, a third optical radiation source 300 may be used, focusing optical radiation on a band differing at least partly from two other sources 206, 208 onto the web 10 obliquely from behind. As in FIG. 2A, when the web 10 is illuminated from a plurality of directions, it is possible to use more than three optical sources.

Thus, the illumination areas of different radiations in different measuring procedures overlap at least partly on the plane of the web 10, and they illuminate a web region that is at least partly common. At most one optical radiation band used in the measurement may be focused on the web 10 from the direction of the normal. Each optical radiation band illuminates the web 10 surface in a flashing manner, i.e. as a pulse. All pulses used in the measurement are focused on the same region of the web within a predetermined time window in such a manner that a movement of the web, i.e. inaccuracy between the images due to feasible non-simultaneous pulses, is not greater than the resolution required from the images.

FIG. 3B illustrates a situation where images 310 and 312 formed of the web at different wavelengths are not precisely aligned. Images that are formed at different wavelengths should have sufficiently similar resolutions and they should be formed of the same web region with a sufficient accuracy. Contributing factors include, for example, mutual alignment inaccuracy $\Delta X_p$ of the images formed on different wavelength bands, and positioning inaccuracy $\Delta X_t = \Delta T \times V$, wherein V is the velocity of the web, due to timing inaccuracy $\Delta T$ of the images formed on different wavelength bands. To have a sufficiently good resolution, $\Delta X_p < R$ and $\Delta X_t < R$ should apply to both inaccuracies, wherein R is the resolution of the image. Thus, the time deviation of two images with respect to one another should be shorter than R/V.

Radiation may also be focused on the web 10 in a direction differing from the direction of the surface normal in such a manner that the radiation is focused on the web as a cone opening or converging perpendicularly from above. Thereby at least some of the rays of each band are focused on the web 10 from a direction other than the direction of the surface normal, thus allowing the measurement to be carried out. On one optical band, radiation may, however, be focused on the web as a perpendicular, collimated radiation.

FIG. 4 shows an embodiment, in which the projector 200, as illustrated in FIG. 2A, comprises chromatic minors. The optical radiation source 206 may comprise, for instance, a plurality of LEDs 400 to 404. The optical radiation sources 208, 300 may also comprise a plurality of LEDs 406 to 416. Of these, the group of LEDs 400 to 404 may emit red light, the group of LEDs 406 to 410 green light and the group of LEDs 412 to 416 may emit blue light. Red, green and blue may form the base of the chromatic coordinate system with visible light. The first chromatic mirror 418 combines the optical band of the optical radiation source 206 with the optical band of the optical radiation source 208. The chromatic minor 418 lets radiation on the optical band of the optical radiation source 206 pass through it but reflects the radiation on the optical band of the optical radiation source 208. The second chromatic minor 420 combines the optical band of the optical radiation source 300 with the bands combined in the chromatic minor 418. The chromatic minor 420 thus lets radiation of the combined bands pass through it, but reflects radiation on the optical band of the optical radiation source 300. Instead of the chromatic minors 418, 420, dichroic beam splitters may be used.

The spatial intensity distribution of each optical radiation source 206, 208, 300 may be formed by masks or the like in connection with, for instance, source-specific optics 422 to 426 or common projection optics 428.

FIG. 5 illustrates different intensity distributions. The vertical axis represents the intensity I on a freely selected axis and the horizontal axis represents the distance from the edge of the illuminated region 210 in the direction x on the web surface. A distribution 500 is a uniform distribution, whereby the intensity is constant in the direction x of the web surface. The intensity distribution 500 may be characteristic of the optical radiation source 206, for instance. In a distribution 502, the intensity first grows linearly but soon becomes non-linear. The intensity distribution 502 may be characteristic of the optical radiation source 208, for instance. In a distribution 504, the intensity varies according to the sine function. An intensity distribution 505 may be characteristic of the optical radiation source 300, for instance.

FIG. 6 shows an example of a two-dimensional intensity distribution in a cartesian x, y coordinate system. The vertical axis represents the distance from a predetermined origin on the web surface in the direction y, and the horizontal axis represents the distance from a predetermined origin on the web surface in the direction x in the illuminated region 210. An intensity distribution 600 may in this example look like a checker board pattern, because the intensity is at its lowest in striped boxes and at its highest in white boxes.

Surface topography refers, for instance, to determination of the surface behaviour in the height direction. The measurement may be used for determining, for example, a line profile in a one-dimensional case and a topographic map in a two-dimensional case, of which both can be either continuous or discontinuous.

After the surface topography of the web 10 has been measured, a controller 126 may control the manufacturing process of paper, paper-board or cardboard on the basis of the determined surface topography. In this case, the controller 126 may control, for example, the surface topography of the web 10 on the basis of the determined surface topography.

The controller 126 may control valves 130 to feed a greater amount of prepared stock more efficiently, if the surface topography is rougher than predetermined. The controller 126 may accordingly control the valves 130 to reduce the stock beating rate by reducing the proportion of prepared stock more efficiently, if the surface topography is smoother than predetermined. The controller 126 may also directly control the beating in order to change the stock beating rate. A change in the stock beating rate may have an effect on the surface topography and possibly on the rest of the paper quality under manufacture.

If the determined surface topography is too rough, the controller 126 may form a control parameter controlling the filter part 102, which may filter away particles the size of which is bigger than predetermined according to the control parameter from the pulp in order to reduce roughness. Accordingly, the controller 126 may form a control parameter controlling the filter part 102, which lets bigger and bigger particles to the web formation process, if the web roughness needs to be increased.

The controller 126 may increase the proportion of the filler TA in the pulp by setting the valve 136 open or opening the valve 136 more, if the surface topography is rougher than predetermined. The controller 126 may accordingly reduce the proportion of the filler in the pulp by closing the valve 136 a little or closing the valve 136 completely, if the surface topography is smoother than predetermined.

The controller 126 may increase the proportion of the filler RA in the pulp by setting the valve 134 open or opening the valve 134 more, if the surface topography is rougher than predetermined. The controller 126 may accordingly reduce the proportion of the filler in the pulp by closing the valve 134 a little or closing the valve 134 completely, if the surface topography is smoother than predetermined.

The controller 126 may control a press load in the press 112 to be greater, if the surface topography is rougher than predetermined. The controller 126 may accordingly control the press load in the press 112 to be smaller, if the surface topography is smoother than predetermined.

The controller 126 may control the press 112 to increase wet drawing, if the measured surface topography of the web is rougher than predetermined. The controller 126 may accordingly control the press 112 to reduce wet drawing if the surface-topographical roughness is smaller than a predetermined value.

The controller 126 may control the drying section 114 to increase the web 10 drawing, if the measured surface topography of the web is rougher than predetermined. The web 10 drawing is increased by making the web 10 tighter between the rolls in the drying section 114. The controller 126 may accordingly control the drying section 114 to reduce the web drawing, if the surface-topographical roughness is smaller than a predetermined value.

By means of the surface topography, the controller 126 may determine a disturbance in the press 112, caused by press felts, and inform the user of the need for a press felt change.

The controller 126 may control the coating section 140 to increase the amount of coating colour, if the surface topography is rougher than predetermined. The controller 126 may accordingly control the coating section 140 to reduce the amount of coating colour, if the surface topography is smoother than predetermined.

The controller 126 may control the coating section 140 to change the coating colour recipe, if the surface topography of the web 10 differs from what was desired.

The controller 126 may increase nip load of a pre- or post-calender 138, 142, if the surface topography is rougher than predetermined. The controller 126 may accordingly reduce the line load of the calender 138, 142, if the surface topography is smoother than predetermined.

The controller 126 may control to increase the frame moisture in the calender 138, 142, if the determined surface topography is rougher than predetermined. The controller 126 may accordingly control to reduce the frame moisture in the calender 138, 142, if the determined roughness of the surface topography needs to be increased.

The controller 126 may control to reduce the surface moisture in the calender 138, 142, if the determined surface topography is rougher than predetermined. The controller 126 may accordingly control to increase the surface moisture in the calender 138, 142, if the determined roughness of the surface topography needs to be increased.

The controller 126 may control to increase the temperature of one or more thermal coils in the calender 138, 142, if the determined surface topography is rougher than predetermined. The controller 126 may accordingly control to reduce the temperature of one or more thermal coils in the calender 138, 142, if the determined roughness of the surface topography needs to be increased.

By means of the surface topography, the controller 126 may determine a disturbance induced by the calender 138, 142. The controller 126 may inform the user of a service need, such as grinding, of one or more rolls in the calender 138, 142, if the surface topography differs from the desired surface topography more than was predetermined. It is sensible to carry out this procedure after the pressing control has been performed.

The controller 126 may generally inform the user of a service need of the system, if the surface topography differs from the desired surface topography more than was predetermined. It may be sensible to carry out this procedure especially after at least one control measure has already been carried out but the deviation remains, some kind of deviation remains, the deviation remains unchanged or the deviation becomes bigger.

FIG. 7 shows a flow chart of a measuring method. In step 700, radiation of at least two different optical bands is focused on one region on the web 10 surface as pulses in such a manner that the illumination areas of the pulses overlap at least partly on the plane of the web 10, at most one optical radiation band is focused on the web 10 from the direction of the normal, the spatial intensity distribution of at least one optical band differs from the uniform distribution, and the intensity distributions of at least two different optical bands differ from one another in a predetermined manner. In step 702, pulse-based images are formed of said web region on said bands of at least two different optical radiations. In step 704, the surface topography of the web 10 is determined on the basis of at least two images formed on the bands of different optical radiations.

FIG. 8 shows a flow chart of a control method. In step 800, radiation of at least two different optical bands is focused on one region on the web 10 surface as pulses in such a manner that the illumination areas of the pulses overlap at least partly on the plane of the web 10, at most one optical radiation band is focused on the web 10 from the direction of the normal, the spatial intensity distribution of at least one optical band differs from the uniform distribution, and the intensity distributions of at least two different optical bands differ from one another in a predetermined manner. In step 802, pulse-based images are formed of said web region on said bands of at least two different optical radiations. In step 804, the surface topography of the web 10 is determined on the basis of at least two images formed on different optical radiation bands. In step 806, the paper manufacturing process is controlled on the basis of the determined surface topography.

Although the invention is described above with reference to the examples according to the attached drawings, it is clear that the invention is not restricted thereto but it may be modified in many ways within the scope of the appended claims.

The invention claimed is:

1. A measuring method for a moving web in a paper or board machine, including focusing optical radiation on the moving web, the method comprising:
producing, by LEDs, pulses of at least two different optical bands within a predetermined time window which is shorter than 2 µs for determining a smallest distinguishable detail of the moving web to have a size of 10 µm,
focusing radiation pulses of the at least two different optical bands on a region in a web surface as pulses so that illumination areas of the pulses overlap at least partly on a plane of the moving web, at most one optical radiation band is focused on the moving web from a normal direction, a spatial intensity distribution of at least one optical band differs from a uniform distribution and intensity distributions of the at least two different optical bands differ from one another in a predetermined manner;
forming pulse-based images of said web region on said bands of at least two different optical radiations; and
determining a surface topography of the moving web based on at least two images formed on the bands of different optical radiations.

2. A method as claimed in claim 1, the method further comprising determining the surface topography of the moving web based on differences in intensity variations in different images.

3. A method as claimed in claim 1, wherein the intensity of said at least one optical band varies along the web surface in at least one direction.

4. A method as claimed in claim 1, the method further comprising forming the optical radiation bands with a group of LEDs including at least three LEDs at different wavelengths.

5. A method as claimed in claim 1, the method further comprising forming successive images by repeatedly focusing optical band radiation pulses on the moving web.

6. A method as claimed in claim 1, the method further comprising focusing the optical radiation bands on the moving web as structural radiations by projecting a predetermined pattern on each optical band onto the moving web.

7. A method as claimed in claim 6, wherein the predetermined patterns on the bands of different optical radiations are parallel-shifted a predetermined distance with respect to one another.

8. A method as claimed in claim 1, wherein in said at least one spatial intensity distribution of the optical band, the intensity varies periodically.

9. A method as claimed in claim 1, wherein in said at least one spatial intensity distribution of the optical band, the intensity varies according to a sine function.

10. A method as claimed in claim 1, the method further comprising focusing the optical radiation on different bands onto the moving web from different directions.

11. A method as claimed in claim 1, the method further comprising focusing the optical radiation on different bands onto the moving web from a same direction.

12. A method as claimed in claim 1, the method further comprising forming the spatial intensity distribution of the at least one optical band by means of a transmission mask.

13. A method as claimed in claim 1, the method further comprising forming the spatial intensity distribution of the at least one optical band by means of a reflection mask.

14. A method as claimed in claim 1, the method further comprising forming the pulse-based images with an RGB camera.

15. A control method for a paper or board manufacturing process, the method comprising focusing optical radiation on a moving web, the method comprising:
producing, by LEDs, pulses of at least two different optical bands within a predetermined time window which is shorter than 2 μs for determining a smallest distinguishable detail of the moving web to have a size of 10 μm,
focusing radiation pulses of the at least two different optical bands on a region in a web surface as pulses so that illumination areas of the pulses overlap at least partly on a plane of the moving web, at most one optical radiation band is focused on the moving web from a normal direction, a spatial intensity distribution of at least one optical band differs from a uniform distribution and intensity distributions of the at least two different optical bands differ from one another in a predetermined manner;
forming pulse-based images of said web region on said bands of at least two different optical radiations; and
determining a surface topography of the moving web based on at least two images formed on the bands of different optical radiations; and
controlling the paper manufacturing process based on the determined surface topography.

16. A method as claimed in claim 15, the method further comprising controlling the web surface topography in the paper manufacturing process based on the determined surface topography.

17. A measuring system for a moving web in a paper or board machine, wherein the system is configured to focus optical radiation on the moving web, and the system comprising:
at least two optical radiation sources comprising LEDs, a camera, and an image-processing unit, of which the at least two optical radiation sources radiate on different optical bands; and
the LEDs are configured to produce pulses of at least two different optical bands within a predetermined time window which is shorter than 2 μs for determining a smallest distinguishable detail of the moving web to have a size of 10 μm,
each LED is configured to focus optical radiation on a region in a web surface as pulses so that illumination areas of the pulses are configured to overlap at least partly on a plane of the moving web, at most one optical radiation band is configured to be focused on the moving web from a normal direction, a spatial intensity distribution of at least one optical band is configured to differ from a uniform distribution and intensity distributions of the at least two different optical bands are configured to differ from one another in a predetermined manner;
the camera is configured to form, on each optical radiation band, pulse-based images of the web surface region on which radiation of at least two different optical bands is focused; and
the image-processing unit is configured to determine a surface topography of the moving web based on at least two images formed on the bands of different optical radiations.

18. A system as claimed in claim 17, wherein the image-processing unit is configured to determine the surface topography of the moving web based on differences in intensity variations in different images.

19. A system as claimed in claim 17, wherein each optical radiation source comprises an intensity shaper, which is configured to produce, in at least one web surface direction, an intensity distribution differing in a predetermined manner on different optical radiation bands.

20. A system as claimed in claim 19, wherein
each intensity shaper comprises a predetermined pattern; and
different optical radiation sources are configured to focus structural radiation on the moving web by projecting the predetermined pattern onto the moving web on each optical band.

21. A system as claimed in claim 20, wherein the predetermined patterns on a different optical band are parallel-shifted a predetermined distance with respect to one another.

22. A system as claimed in claim 17, wherein at least one optical radiation source is laser.

23. A system as claimed in claim 22, wherein
the optical radiation sources are configured to focus periodic pulses, and
the camera is configured to form successive images based on the periodic pulses.

24. A system as claimed in claim 17, wherein the optical radiation sources are configured to focus structural radiation on the moving web by projecting a predetermined pattern on each optical band onto the moving web.

25. A system as claimed in claim 24, wherein the predetermined patterns on the different optical bands are parallel-shifted a predetermined distance with respect to one another.

26. A system as claimed in claim 17, wherein in said at least one spatial intensity distribution of the optical band, the intensity varies periodically.

27. A system as claimed in claim 17, wherein in said at least one spatial intensity distribution of the optical band, the intensity varies according to a sine function.

28. A system as claimed in claim 17, wherein the optical radiation sources are configured to focus the optical radiation on different bands onto the moving web from different directions.

29. A system as claimed in claim 17, wherein the optical radiation sources are configured to focus the optical radiation on different bands onto the moving web from a same direction.

30. A system as claimed in claim 17, wherein the system comprises a transmission mask for forming the spatial intensity distribution of the at least one optical band.

31. A system as claimed in claim 17, wherein the system comprises a reflection mask for forming the spatial intensity distribution of the at least one optical band.

32. A system as claimed in claim 17, wherein the camera is an RGB camera.

33. A control system for a paper or board manufacturing process, wherein the system is configured to focus optical radiation on a moving web, and the system comprising:
- at least two optical radiation sources comprising LEDs, a camera, an image-processing unit, and a controller, of which at least two optical radiation sources radiate on different optical bands; and
- LEDs are configured to produce pulses of at least two different optical bands within a predetermined time window which is shorter than 2 µs for determining a smallest distinguishable detail of the moving web to have a size of 10 µm,
- each LED is configured to focus optical radiation on a region in a web surface as pulses so that illumination areas of the pulses are configured to overlap at least partly on a plane of the moving web, at most one optical radiation band is configured to be focused on the moving web from a normal direction, a spatial intensity distribution of at least one optical band is configured to differ from a uniform distribution and intensity distributions of the at least two different optical bands are configured to differ from one another in a predetermined manner;
- the camera is configured to form, on each optical radiation band, pulse-based images of the web surface region on which radiation of at least two different optical bands is focused;
- the image-processing unit is configured to determine a surface topography of the moving web based on at least two images formed on the bands of different optical radiations; and
- the controller is configured to control the paper manufacturing process based on the determined surface topography.

34. A control system as claimed in claim 33, wherein the controller is configured to control the web surface topography in the paper manufacturing process based on the determined surface topography.

35. A control system as claimed in claim 33, wherein
the controller is configured to increase a stock beating rate, if the surface topography is rougher than a predetermined value, and
the controller is configured to reduce the stock beating rate, if the surface topography is smoother than a predetermined value.

36. A control system as claimed in claim 33, wherein
the controller is configured to control a filter part to filter away particles, a size of the particles is bigger than determined, by means of a control, if the surface topography is rougher than a predetermined value, and
the controller is configured to control the filter part to let bigger particles pass to a web formation process, if a web roughness needs to be increased.

37. A control system as claimed in claim 33, wherein
the controller is configured to increase a proportion of a filler in a pulp, if the surface topography is rougher than a predetermined value, and
the controller is configured to reduce the proportion of the filler in the pulp, if the surface topography is smoother than a predetermined value.

38. A control system as claimed in claim 33, wherein
the controller is configured to increase press load, if the surface topography is rougher than a predetermined value, and
the controller is configured to reduce press load, if the surface topography is smoother than a predetermined value.

39. A control system as claimed in claim 38, wherein
the controller is configured to determine, based on the surface topography, a disturbance caused by press felts and to inform a user of a change of press felts.

40. A control system as claimed in claim 33, wherein
the controller is configured to increase wet drawing, if the surface topography is rougher than a predetermined value, and
the controller is configured to reduce wet drawing, if the roughness is smaller than a predetermined value.

41. A control system as claimed in claim 33, wherein
the controller is configured to increase drawing in a drying section, if the surface topography is rougher than a predetermined value, and
the controller is configured to reduce drawing, if the roughness is smaller than a predetermined value.

42. A control system as claimed in claim 33, wherein the controller is configured to increase an amount of coating colour, if the surface topography is rougher than a predetermined value.

43. A control system as claimed in claim 33, wherein the controller is configured to reduce an amount of coating colour, if the surface topography is smoother than a predetermined value.

44. A control system as claimed in claim 33, wherein the controller is configured to change a coating colour recipe, if the surface topography differs from what was predetermined.

45. A control system as claimed in claim 33, wherein the controller is configured to increase a line load of a calender, if the surface topography is rougher than a predetermined value.

46. A control system as claimed in claim 33, wherein the controller is configured to increase a frame moisture in a calender, if the surface topography is rougher than a predetermined value.

47. A control system as claimed in claim 33, wherein the controller is configured to reduce a surface moisture in a calender, if the surface topography is rougher than a predetermined value.

48. A control system as claimed in claim 33, wherein the controller is configured to increase a temperature in a calendar, if the surface topography is rougher than a predetermined value.

49. A control system as claimed in claim 33, wherein the controller is configured to determine, by means of the surface topography, a disturbance caused by at least one roll in a calender and to inform a user of a need for servicing said at least one roll.

50. A control system as claimed in claim 33, wherein the controller is configured to inform a user of a service need, if, also after the controller measures, the surface topography differs from a desired surface topography more than what was predetermined.

* * * * *